United States Patent [19]
Laursen

[11] Patent Number: 5,864,232
[45] Date of Patent: Jan. 26, 1999

[54] MAGNETIC FLUX PIPE INSPECTION APPARATUS FOR ANALYZING ANOMALIES IN A PIPELINE WALL

[75] Inventor: Poul Laursen, Toronto, Canada

[73] Assignee: Pipetronix, Ltd., Concord, Canada

[21] Appl. No.: 701,662

[22] Filed: Aug. 22, 1996

[51] Int. Cl.[6] ............................ G01N 27/72; G01N 27/82
[52] U.S. Cl. ............................................ 324/220; 324/242
[58] Field of Search ..................................... 324/220, 219, 324/221, 226, 262, 243, 242, 236, 237, 238, 228

[56] References Cited

U.S. PATENT DOCUMENTS

| | | | |
|---|---|---|---|
| 4,088,946 | 5/1978 | Charles et al. | 324/220 |
| 4,675,604 | 6/1987 | Moyer et al. | 324/220 |
| 4,789,827 | 12/1988 | Bergander | 324/220 |
| 5,279,168 | 1/1994 | Timm | 324/220 |
| 5,313,838 | 5/1994 | Gondard et al. | 324/220 |
| 5,454,276 | 10/1995 | Wenicke | 324/220 |
| 5,532,587 | 7/1996 | Downs et al. | 324/220 |
| 5,565,633 | 10/1996 | Wernicke | 324/220 |
| 5,623,203 | 4/1997 | Hosohara et al. | 324/220 |

*Primary Examiner*—Jay M. Patidar
*Attorney, Agent, or Firm*—Sherman and Shalloway

[57] ABSTRACT

An apparatus for analyzing anomalies such as cracks, corrosion and the like in a pipeline wall is provided. The apparatus is formed of one or more cylindrical body sections. A series of magnetizing units are mounted around the circumference of the body. Each magnetizing unit is formed by a backing bar, brushes which are capable of inducing a magnetic field, sensors which are capable of measuring magnetic flux leakage caused by anomalies in the wall and bearing wheels which reduce wear on the brushes and sensors. The backing bar is flexibly mounted on the body so that it can follow the contour of the pipeline wall as the apparatus moves through the pipeline. The backing bar has steel-containing brushes mounted on either end atop magnets of opposite polarities such that a magnetic field may be transmitted to the pipeline wall. The brushes are ideally formed by steel cables encased in polyurethane and mounted on a steel shell. The sensors are mounted in the central part of the backing bar, between the brushes. The sensors preferably have a parallelogram cross-sectional shape and are molded of polyurethane or other suitable material so that they are flexible enough to follow the contour of the pipeline wall as the apparatus travels through the pipeline and, hence, maintain the orientation of the sensing element in the sensor body in relation to the pipeline wall. A wear plate and wear pads may be mounted on top of the sensor body for reducing wear on the sensor.

15 Claims, 9 Drawing Sheets

MAGNETIC FLUX PIPE INSPECTION APPARATUS FOR ANALYZING ANOMALIES IN A PIPELINE WALL

FIELD OF THE INVENTION

This invention relates generally to apparatus known as "intelligent pigs" used as diagnostic tools in oil and gas pipelines and, more specifically, to pigs which use magnetic fields to diagnose defects and other anomalies in pipeline walls.

BACKGROUND OF THE INVENTION

In maintaining the structural integrity of a pipeline, it is important to be able to detect and repair anomalies in the pipeline wall. For present purposes, anomalies include defects such as cracks, pitting, corrosion and dents. In particular, it is important to be able to determine the location of the anomaly, the type of the anomaly and the geography of the anomaly (i.e. its shape and size).

When it is desired to test the structural integrity of a pipeline, a pig may be placed in the pipeline where it is then propelled through the pipeline by the product in the line, such as oil or gas. The pig is typically fitted with urethane "cups" near its front end to seal the annulus between the pig and the pipeline wall, thus preventing pipeline fluid from flowing through the annulus. Pressure behind the pig builds up to the point that the pig begins to move. The differential pressure created across the front and rear of the cups keeps the pig moving through the line.

As the pig moves through the pipeline, it can gather data concerning anomalies in the pipeline wall. If this information can be measured by the pig, stored and later retrieved, it can then be analyzed so as to permit remedial action to be taken.

It is known to use a pig in combination with magnetic flux leakage (MFL) technology to detect defects in pipeline walls. The principle of MFL is based on magnetizing the pipe wall and using sensors to measure the leakage field generated by anomalies in the pipe wall material. For example, if no anomalies are present, the magnetic field will be continuous and there will be no leakage to be detected. If there is an anomaly such as a crack, the magnetic field in the pipeline wall will be interrupted and the stray fields which are generated will provide useful information concerning the anomaly.

Although there are pigs, including pigs manufactured by the assignee of the present application, which do an adequate job of detecting and measuring anomalies in pipeline walls, such pigs have limitations which can impact upon the quality of the measurements obtained. The main drawback with the prior art pigs is that they are not capable of generating sufficient magnetic power for transmission through relatively thick pipeline walls. In any situation, the requisite magnetic field is proportional to the thickness of the pipe wall; that is, the thicker the wall is, the stronger the field has to be to penetrate the wall. The prior art pigs are, for the most part, limited to pipeline walls of approximately 12 mm (about ½ inch) thickness given that these pigs are not designed to generate the requisite magnetic field for thicker pipeline walls.

Another limitation of the prior art pigs is the spacing (and therefore the number) of sensing elements which are mounted around the circumference of the pig. For example, if the distance between the sensing elements is 15 mm, as is the case with the previous generation of pigs manufactured by the assignee of the present application, then a defect could be up to 12 mm in diameter and not always be detected correctly.

The positioning of the sensors in relation to the pipeline wall also limits the depth of defect that can be sensed. The prior art methods of mounting the sensing element, the element which actually measures the magnetic field, place limitations on how close the sensing element can be placed in relation to the pipeline wall. This results in a less than optimum signal-to-noise ratio and, hence, a less than optimum MFL reading. For example, a defect with less than 10% wall thickness material loss typically cannot be picked up by these sensors.

Yet another limitation of the prior art is the length of pipeline that the pigs can inspect. This limitation is dictated not only by the amount of data that the recording units can collect and the amount of battery power available to keep the recorders going, but also by the fact that the mechanical components wear while riding for a prolonged period of time against the pipe wall. The components which transmit the magnetic field to the pipeline wall and the sensors themselves are in constant contact with the pipeline wall and therefore tend to wear over time.

There has therefore developed a need for a pig which is capable of detecting and diagnosing anomalies in relatively thick pipeline walls and which is capable of achieving a higher than previously attained level of accuracy in the measurement of magnetic flux leakage in any size of pipeline wall. There has also developed a need for a pig on which the components which generate the magnetic field and the components which measure the MFL are less prone to wear than the pigs of the prior art so that the pigs may be more suitable for long run applications or a series of short runs without the need for refurbishments between runs.

SUMMARY OF THE INVENTION

In a first aspect, the present invention provides an apparatus for analyzing anomalies in a pipeline wall comprising: a body of generally cylindrical shape; means for supporting the body in relation to the pipeline wall; means for propelling the body through the pipeline; means for providing electrical power to the body; means for storing data; means mounted on the body for generating and transmitting a magnetic field through portions of the pipeline wall adjacent the body; means for measuring magnetic flux leakage adjacent the body caused by anomalies in the pipeline wall; means for transmitting the magnetic flux leakage measurements to the data storage means; and a plurality of wheels mounted on the body adjacent the magnetic field generating means for bearing against the pipeline wall as the body moves through the pipeline so as to reduce wear on the magnetic field generating means and the magnetic flux leakage measuring means.

The apparatus may further comprise a plurality of bars, each bar flexibly mounted on the body to allow the bar to move radially inwardly and radially outwardly to provide clearance for the apparatus in the event that it encounters obstructions as it travels through the pipeline; and wherein the means for generating and transmitting a magnetic field to the pipeline wall, the means for measuring magnetic flux leakage and the bearing wheels are mounted on the bars.

The magnetic flux leakage measuring means may comprise: a sensor body; at least one sensing element, which is capable of sensing absolute magnetic field, housed within the sensor body; and wherein the sensor body is flexible such that it can follow the contour of the pipeline wall as the apparatus moves through the pipeline and hence keep the sensing element in a substantially constant orientation with respect to the pipeline wall.

The apparatus may further comprise non-ferromagnetic means, mounted on the upper surface of the sensor body, for reducing wear on the sensor body and for protecting the sensing element from damage.

The wear reducing means and the sensing element may be bonded together to form an integral unit. The wear reducing means may comprise a wear plate and at least one wear pad. The wear plate may be shaped to generally follow the contour of the pipeline wall.

The sensor body may be in the shape of a parallelogram in its cross-section. The sensor body may be a one piece polymer which is petrochemical resistant, temperature resistant in the range 0° C. to 80° C. and can withstand pressures of up to about 3700 pounds per square inch. For example, the sensor body could be constructed of polyurethane.

The means for generating and transmitting a magnetic field to the pipeline wall may comprise: a first steel-containing brush situated above a first magnet on one end of each bar; a second steel-containing brush situated above a second magnet of the opposite polarity to the first magnet on the other end of the bar; and wherein the upper surfaces of the brushes come into close contact with the pipeline wall at all times.

The brushes may comprise a plurality of steel cables encased and bonded in a plastic resin and mounted on a steel shell. For example, the plastic resin may be polyurethane.

In another aspect, the invention provides an apparatus for analyzing anomalies in a pipeline wall comprising: a first section of generally cylindrical shape housing means for providing electrical power to the apparatus; a second section of generally cylindrical shape for storing data retrieved by the apparatus; a third section of generally cylindrical shape having means for generating and transmitting a magnetic field through portions of the pipeline wall adjacent the third section and means for sensing magnetic flux leakage adjacent the third section caused by anomalies in the pipeline wall; a plurality of wheels mounted on the third section for bearing against the pipeline wall as the apparatus moves through the pipeline so as to prevent wear on the magnetic field generating and transmitting means and the magnetic flux sensing means; means for supporting the sections in relation to the pipeline wall; means for propelling the sections through the pipeline; means for transmitting the magnetic flux leakage measurements to the data storage means; a plurality of wheels mounted on the third section adjacent the magnetic field generating means for bearing against the pipeline wall as the apparatus moves through the pipeline so as to reduce wear on the magnetic field generating means and the magnetic flux leakage measuring means; and wherein adjacent sections are connected by flexible links so as to permit movement of the apparatus through bends and restrictions in the pipeline. The sections may be arranged in any order.

BRIEF DESCRIPTION OF THE DRAWINGS

For a better understanding of the present invention and to show more clearly how it may be carried into effect, reference will now be made by way of example to the accompanying drawings, which show an apparatus according to the preferred embodiment of the present invention and in which.

DETAILED DESCRIPTION OF THE PREFERRED EMBODIMENTS

Figure 1:
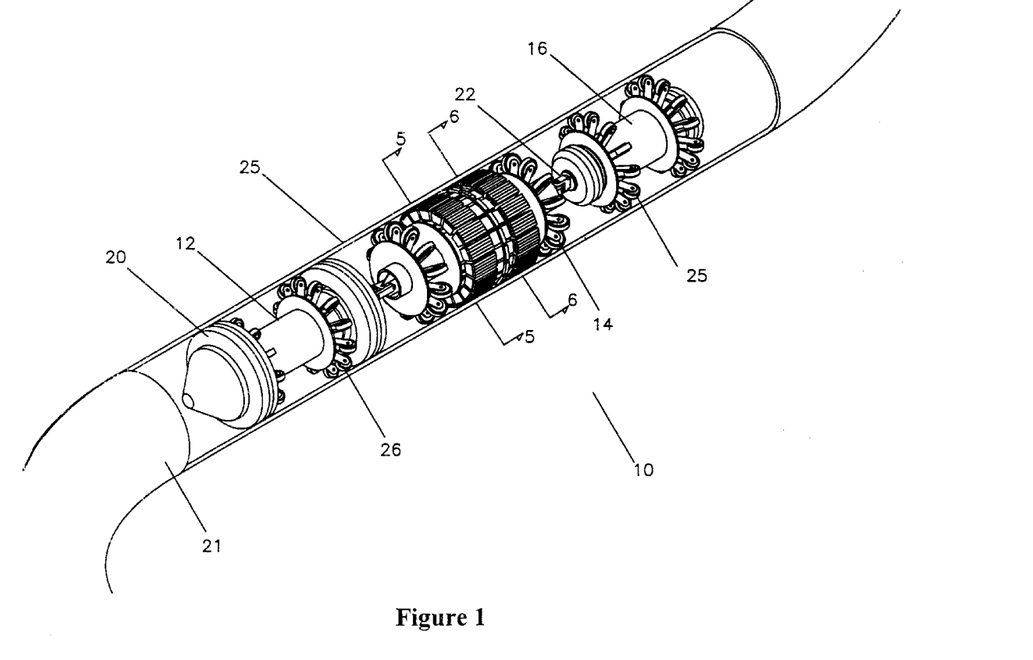
FIG. 1 is a diagrammatic illustration of an apparatus for analyzing anomalies in a pipeline wall according to the preferred embodiment of the present invention.

Referring now to FIG. 1, an apparatus 10 for analyzing anomalies in pipeline walls, or a "pig" as it is commonly known, comprises a first section 12, a second section 14 and a third section 16. In the embodiment illustrated, the first section 12 houses the batteries or other means for providing electrical power to the apparatus. Annular seals 20, or "cups" as they are commonly known, are mounted around the circumference of the first section for sealing the annulus between the first section and the pipeline wall. Accordingly, the flow of pipeline fluid such as natural gas or oil is blocked by the annular seal, resulting in the propulsion of the pig through the pipeline.

The second section 14 has mounted on it means for magnetizing the pipeline wall 21 and means for detecting the resulting magnetic flux leakage. These means are described in more detail below. The third section 16 houses the data acquisition system for the pig. Data concerning the analysis of anomalies in the pipeline wall may be transmitted from the sensors to the data acquisition system, stored and subsequently retrieved for analysis upon removal of the pig from the pipeline.

Adjacent sections are connected by a flexible link 22 such as a universal joint so as to permit movement of the pig through bends in the pipeline. The order of the three sections in the pipeline is not important. The only requirement is that the annular seal 20 must be mounted on the section which is the furthest downstream when the pig is placed in the pipeline.

Furthermore, it is not essential that the apparatus be formed of three sections. In fact, it is possible to house the electrical means, the magnetizing means and the data acquisition system all in a single section. It may be preferable, however, to house these systems in separate sections when constructing a pig for use in relatively thick pipelines as it may be somewhat more difficult to house all of the above elements in a single section for such applications.

Suspension wheels 26 are mounted around the circumference and on opposite ends of each section for bearing against the pipeline wall so as to stabilize the pig within the pipeline and facilitate the movement of the pig through the pipeline. Other means for stabilizing the pig within the pipeline are possible. For example, cups can be used to stabilize the pig. Also, it is not essential that stabilizing means be mounted on each section. It is sufficient if stabilizing means are mounted on the section which is the furthest downstream and the section which is the furthest upstream when the pig is inserted in the pipeline.

Figure 2:
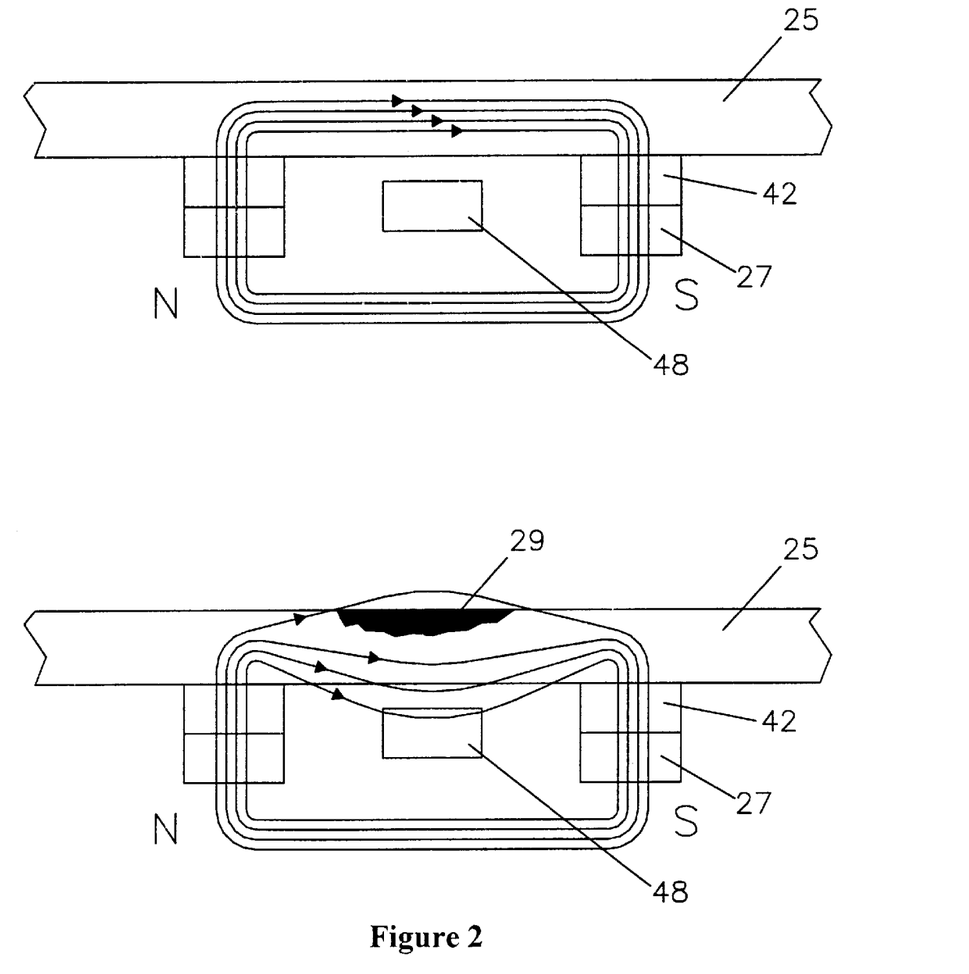
FIG. 2 is a diagram illustrating the principle of magnetic flux leakage as measured by the present invention.
Figure 3:
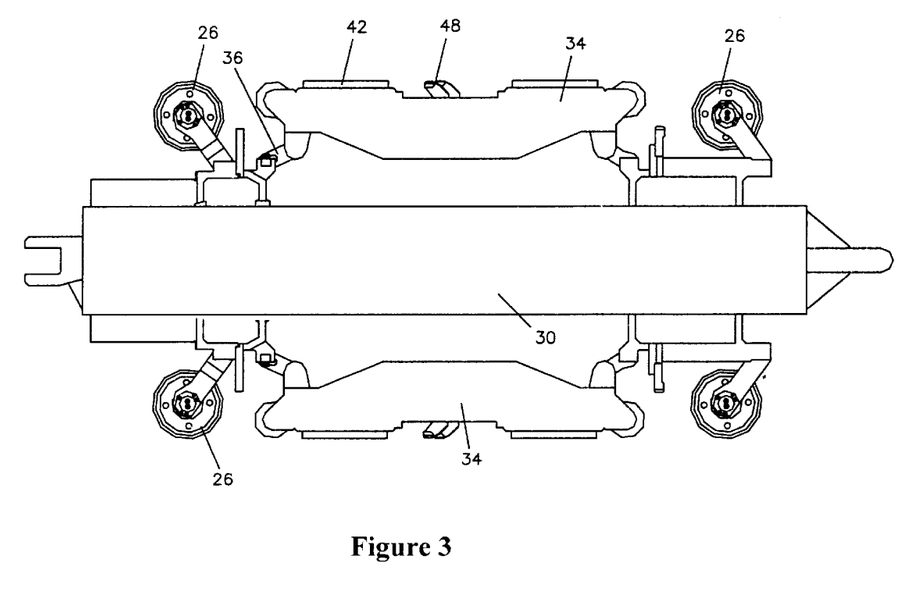
FIG. 3 is a side view of the magnetizing section of the apparatus shown in FIG. 1.
Figure 4:
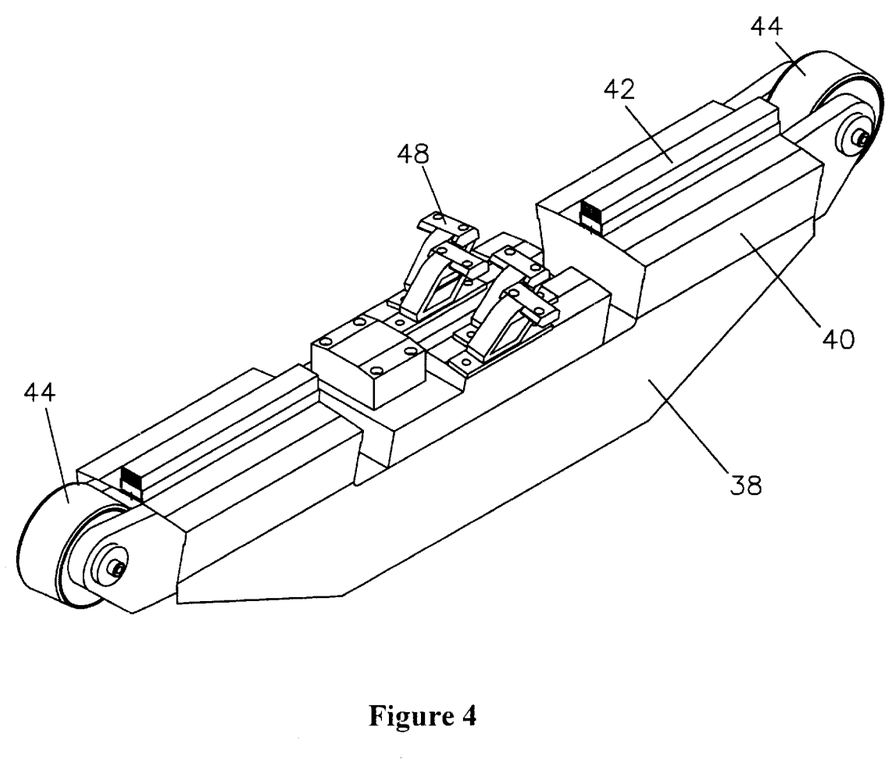
FIG. 4 is an axonometric view of the magnet unit of the apparatus shown in FIG. 1.
Figure 5:
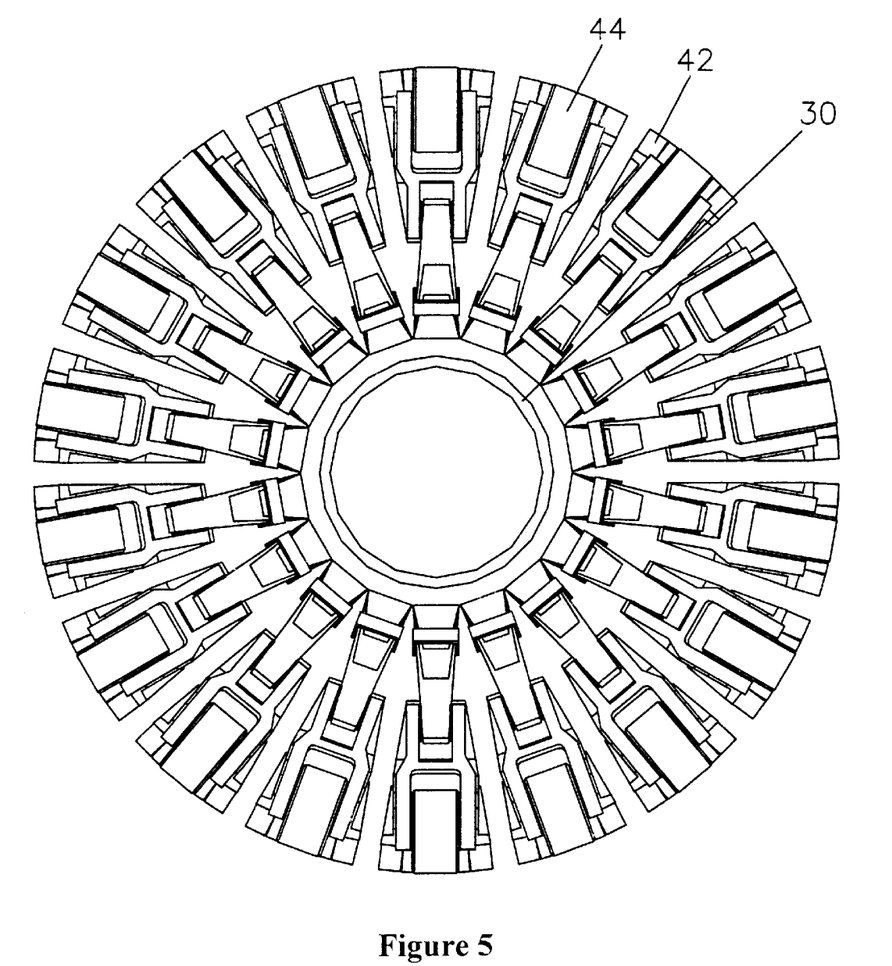
FIG. 5 is a cross-sectional view, taken along the line 5—5 in FIG. 1, showing the arrangement of the wheels and brushes on the magnetizing section of the apparatus of FIG. 1.
Figure 6:
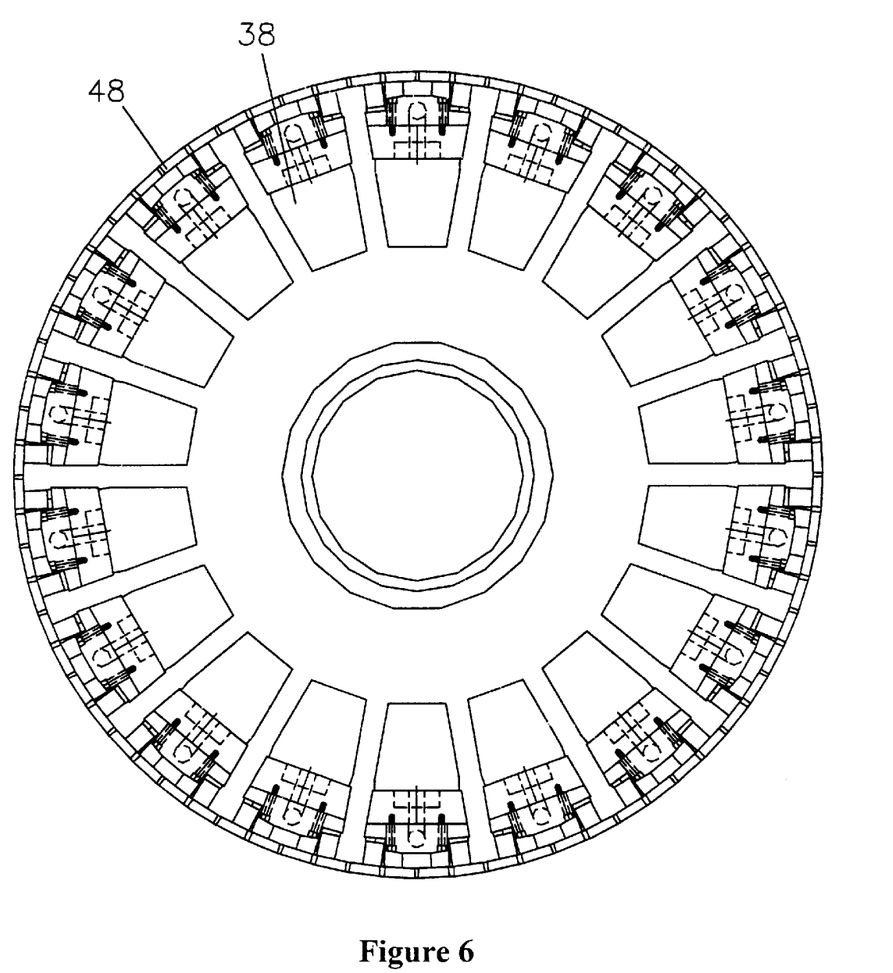
FIG. 6 is a cross-sectional view taken along the line 6—6 in FIG. 1 showing the arrangement of the magnet units and sensors on the magnetizing section.

Referring now to FIGS. 2 through 4, the principle of MFL is illustrated as it applies to the present invention. The present invention uses magnet 27 backed brushes 42 to magnetize the pipe wall 25. Sensors 48 which are mounted between arrays of brushes detect the leakage field generated by anomalies in the pipeline wall material. If the pipeline wall has no anomalies or defects, the magnetic flow is undisturbed and the sensor detects no field (as illustrated in the upper schematic of FIG. 2). If, however, an anomaly 29 is present, the field is disturbed and the sensor picks up this stray field and sends a signal back to the recording unit (as illustrated in the lower schematic of FIG. 2).

The strength of the MFL signal that results from an anomaly is affected by many parameters, such as the magnetizing force, pipe wall magnetization, anomaly geometry, anomaly type, etc. The problem is that not all of these parameters are known and controlled, which makes it difficult to obtain an accurate anomaly sizing.

Referring now to FIGS. 3 and 4, the magnetizing section (the second section 14 in FIG. 1) is built up from a central body 30, which is supported by a plurality of suspension wheels 26 mounted near opposite ends of the magnetizing section and around the circumference of the magnetizing section. These wheels support the entire magnetizing section against the pipeline wall for movement of the section through the pipeline. A plurality of suspended magnet unit arrays 34 are mounted on the center part of the section and around the circumference of the section. Each of the magnet unit arrays is suspended on biasing means 36, such as springs or the like, so that it can travel towards the center of the pig where necessary, thus reducing the pig's diameter and enabling the pig to pass through restrictions and bends in the pipeline.

As best shown in FIG. 4, the magnet unit array 34 consists of a backing bar 38 and two end clusters which contain a magnet or clusters of magnets 40. The magnets in opposite end clusters are of opposite polarities so as to induce a magnetic field in the pipeline wall. Each end cluster has a series of brushes 42 mounted on top. The construction of these brushes is described in more detail below. For present purposes it is sufficient to note that these brushes contain steel cables or other arrangements of steel material in contact with a steel shell along the base of the brush for making contact with the magnet below and, hence, for generating the necessary magnetic field.

For convenience of illustration, only the middle of five brushes has been depicted on each end cluster of FIG. 4. Other numbers and shapes of brushes could be used without departing from the spirit of the present invention. When the pig travels through the pipeline, the upper surfaces of these brushes are in substantial contact with the pipeline wall during the run and therefore transmit the necessary magnetic flux to the pipeline wall.

As best shown in FIG. 4, to reduce the amount of wear these brushes see during a run, a bearing wheel 44 is mounted to each end of the magnet unit. An additional advantage is that these wheels maintain a substantially constant distance between the magnet units and the pipeline wall so that a substantially constant magnetic field is produced during the pig's run.

The sensors 48 that pick up the anomalies in the pipeline wall are positioned in an array located between the two end clusters on the magnet unit and hence between the arrays of brushes.

Figure 7:
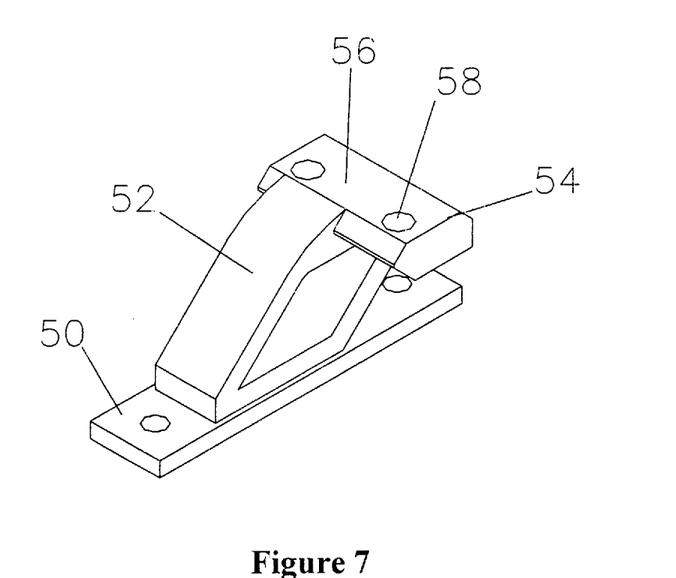
FIG. 7 is an elevational view of a sensor.
Figure 8:
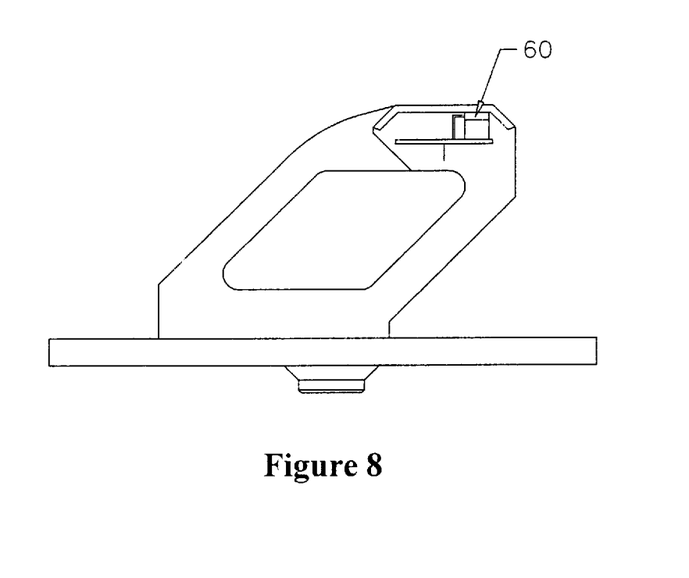
FIG. 8 is a side view, partly in section, of a sensor.
Figure 9:
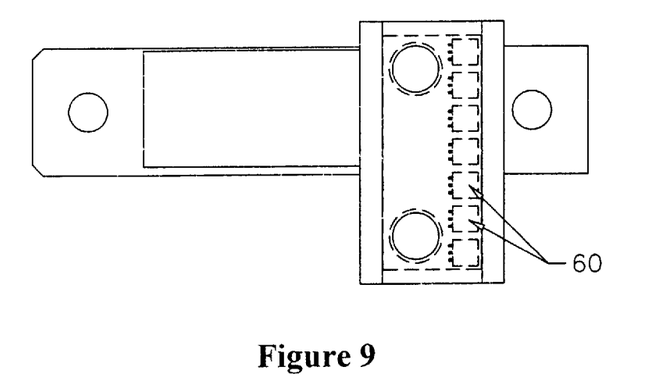
FIG. 9 is a bottom view, partly in section, of a sensor.

The sensors may be a polyurethane molded unit. As best shown in FIGS. 7 through 9, the sensors contain a base plate 50 mounting the sensor to the backing bar, sensor body 52, top plate 54, wear plate 56, wear pads 58 and sensing elements 60. The sensing elements make the actual measurement of the MFT and therefore must be capable of sensing absolute magnetic field as opposed to sensing elements which are only capable of detecting changes in magnetic field.

Preferably, these components are all bonded together in the molding process. By eliminating the need for a mechanical attachment of the sensing elements to the wear plate, the present invention is able to locate the sensing element as close to the pipeline wall as possible. This arrangement results in an improved signal-to-noise ratio and, hence, improved performance of the apparatus.

Although the sensor shown in FIGS. 7 through 9 illustrates a top plate and a wear plate which are oriented perpendicular to the base plate, it is not necessary that this particular arrangement be used. For example, the top plate and the wear plate could be arranged parallel to the base plate such that these plates form the top surface of the parallelogram shape of the sensor.

As best seen in FIGS. 4 and 9, however, there are certain advantages to the shape and arrangement of sensors depicted in these drawings. As shown in FIG. 9, the sensing elements 60 are equidistantly spaced apart in the top plate 54. By arranging the sensors as shown in FIG. 4, with their top plates staggered, it is possible to position the sensing elements such that they are spaced equidistantly around the circumference of the apparatus. It is also possible to position the sensing elements more closely together than would otherwise be possible. The advantage of being able to position the sensing elements more closely together and, hence, being able to position more sensing elements around the pig is that a higher degree of resolution in the signal detected by the elements can be achieved. The advantage of being able to position the sensing elements equidistantly around the pig is that a more constant signal will be detected by the sensing elements. For example, a constant spacing of 6 mm (about ¼ inch) or less, as measured between the centers of adjacent sensing elements, has been found to provide an improved degree of resolution in the signal detected by the sensing elements. It will be appreciated that there are other arrangements of the sensors and the sensing elements which will result in the sensing elements being positioned equidistantly, or nearly so, around the circumference of the pig.

Preferably, the sensor body is shaped as a parallelogram. It has been found that this shape is particularly useful in maintaining the sensing elements close to the pipeline wall and in maintaining the orientation of the sensing elements relative to the pipeline wall.

Accordingly, the parallelogram shape of the sensor body results in improved accuracy of the sensor signal and also results in consistency of the quality of the signal so that differences in the signal at different locations in the pipeline can be interpreted as being due to anomalies rather than being attributable to bends or restrictions in the pipeline.

Preferably, the sensor body is a one piece polymer such as polyurethane which is petrochemical resistant so that it will not be broken down by chemicals in the pipeline. The sensor body is also preferably temperature resistant in the range 0° C. to 80° C. and can withstand pressures of up to about 3700 pounds per square inch.

A sensor as described in accordance with this preferred embodiment has the advantages of being flexible enough to follow the contours of the pipeline wall so as to maintain the sensing elements in the same position in relation to the wall and yet being durable enough to withstand long runs in the pipeline.

Figure 10:
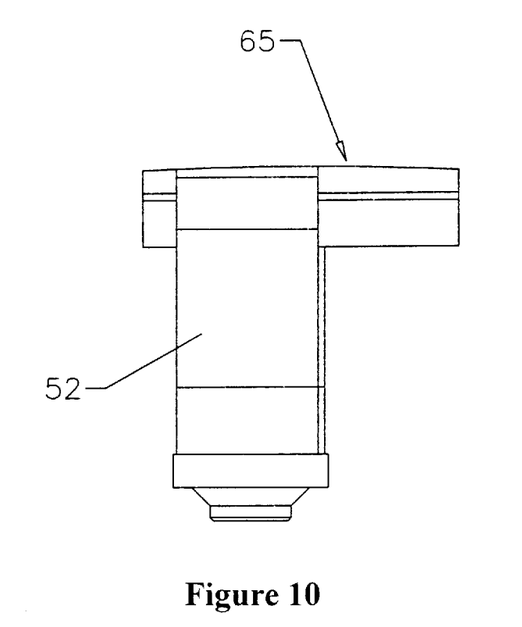
FIG. 10 is a front view of a sensor.

As best shown in FIG. 10, the wear plate 56 is preferably curved along its upper surface 65 to follow the curvature of the pipeline. This design places the sensing elements closer to the pipeline wall surface than previously possible. As a result, there is an improved signal-to-noise ratio and an improved reading is achieved. The wear pads, which may be constructed of ceramic material or the like, reduce the amount of wear on the sensor thus giving it a longer life. The means for reducing wear on the sensors, such as the wear plate and the wear pads, must be non-ferromagnetic so as not to interfere with the signals being recorded by the sensing elements.

Figure 11:
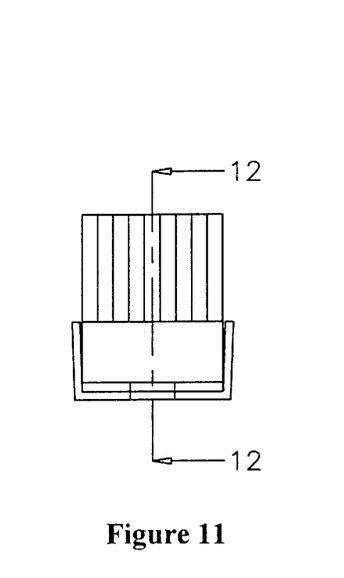
FIG. 11 is an end view of a brush.
Figure 12:
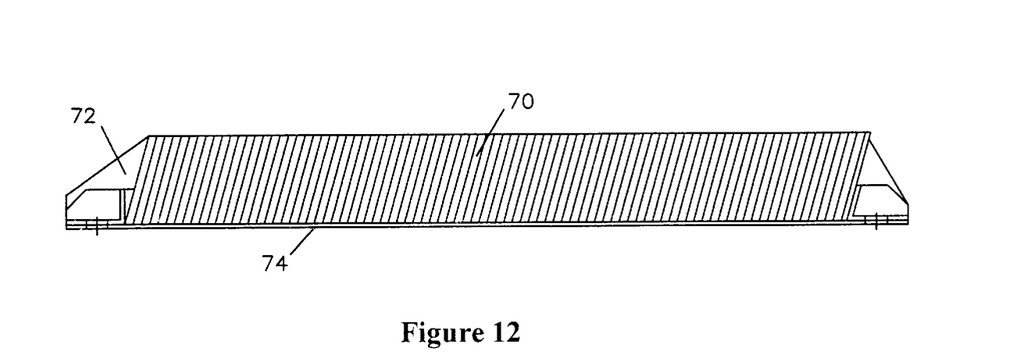
FIG. 12 is a cross-sectional side view of a brush taken along the line 12—12 of FIG. 11.

Referring now to FIGS. 11 and 12, the brushes comprise steel cables 70 encased in polyurethane 72 mounted on a steel shell 74. This composite has a much improved wear capacity with improved magnetic transmitting properties so as to permit the magnetization of thicker pipeline walls than the pigs of the prior art. This is due to the increased density which is achieved by closer packing of the steel cables which, in turn, is achieved by the bonding of the steel cables in polyurethane.

The pig of the present invention is now described by reference to its operation in a pipeline. The first step in arriving at anomaly sizing is to achieve even magnetization in the pipe wall. This is accomplished by designing a high efficiency magnetizing unit which is able to transmit a high amount of magnetic flux into the pipe wall.

The next step is to measure and store the leakage signal correctly. To do this, the pig of the present invention has higher resolution than is known in the prior art due to the construction and spacing of the sensors. It has been found that if the sensors of the present invention are more closely spaced apart, they can detect smaller and shallower defects. A signal from the sensor is taken at predetermined intervals along the length of the pipeline. All the data is then stored in the data acquisition system for later retrieval and analysis upon removal of the pig from the pipeline.

The final step in anomaly sizing is to interpret the recorded signal with as many known parameters as possible. This is accomplished by running the tool over a section of pipe with known defects and correlating the signals received to the actual defect. In this way an unknown defect's size can be determined through these calibration curves.

With a more efficient magnet unit design, higher levels of magnetization are achieved. The better brush design can transmit this magnetic field into the pipe wall more effectively. Closer spaced sensors and better sensor positioning increases the sensitivity of the tool. This means that much smaller anomalies can be detected in much thicker wall pipe than was previously possible.

The addition of bearing wheels to the magnet unit and the incorporation of wear pads to the sensors greatly reduce the wear on the brushes and sensors. This, in turn, makes the new design more suitable to long run applications. Conversely, the tool can do many more short runs with less down time in between, since major refurbishments between runs are no longer required.

This description is made with reference to the preferred embodiment of the invention. However, it is possible to make other embodiments that employ the principles of the invention and that fall within its spirit and scope as defined by the following claims.

What is claimed is:

1. An apparatus for analyzing anomalies in a pipeline wall comprising:
    a body of generally cylindrical shape;
    means for supporting the body in relation to the pipeline wall;
    means for propelling the body through the pipeline;
    means for providing electrical power to the body;
    means for storing data;
    a plurality of bars disposed circumferentially around the body, each bar flexibly mounted on the body to allow the bar to move radially inwardly and radially outwardly to provide clearance for the apparatus in the event that it encounters obstructions as it travels through the pipeline;
    means mounted on the bars for generating and transmitting a magnetic field through portions of the pipeline wall adjacent the body;
    means mounted on the bars for measuring magnetic flux leakage adjacent the body caused by anomalies in the pipeline wall;
    means for transmitting the magnetic flux leakage measurements to the data storage means; and
    a plurality of wheels mounted on the bars adjacent the magnetic field generating means for bearing against the pipeline wall as the body moves through the pipeline so as to reduce wear on the magnetic field generating means and the magnetic flux leakage measuring means.

2. The apparatus of claim 1, wherein the magnetic flux leakage measuring means comprise:
    a sensor body;
    at least one sensing element, which is capable of sensing absolute magnetic field, housed within the sensor body;
    and wherein the sensor body is flexible such that it can follow the contour of the pipeline wall as the apparatus moves through the pipeline and hence keep the sensing element in a substantially constant orientation with respect to the pipeline wall.

3. The apparatus of claim 2, wherein the apparatus further comprises non-ferromagnetic means, mounted on the upper surface of the sensor body, for reducing wear on the sensor body and for protecting the sensing element from damage.

4. The apparatus of claim 3, wherein the wear reducing means and the sensing element are bonded together to form an integral unit.

5. The apparatus of claim 3, wherein the wear reducing means are shaped to generally follow the contour of the pipeline wall.

6. The apparatus of claim 3, wherein the wear reducing means comprise a wear plate and at least one wear pad.

7. The apparatus of claim 2, wherein the sensing elements are positioned generally equidistantly around the circumference of the body.

8. The apparatus of claim 7, wherein the distance between the centers of adjacent sensing elements is less than 6 mm.

9. The apparatus of claim 2, wherein the sensor body's cross-sectional shape is generally a parallelogram.

10. The apparatus of claim 9, wherein the sensor body is a one piece polymer which is petrochemical resistant, temperature resistant in the range 0° C. to 80° C. and can withstand pressures of up to about 3700 pounds per square inch.

11. The apparatus of claim 10, wherein the sensor body is constructed of polyurethane.

12. The apparatus of claim 1, wherein the means for generating and transmitting a magnetic field to the pipeline wall comprise:

a first steel-containing brush situated above a first magnet on one end of each bar;

a second steel-containing brush situated above a second magnet of the opposite polarity to the first magnet on the other end of the bar;

and wherein the upper surfaces of the brushes come into relatively close contact with the pipeline wall at all times.

13. The apparatus of claim 12, wherein the brushes comprise a plurality of steel cables encased and bonded in a plastic resin and mounted on a steel shell.

14. The apparatus of claim 13, wherein the plastic resin is polyurethane.

15. An apparatus for analyzing anomalies in a pipeline wall comprising, in any order,:

a first section of generally cylindrical shape housing means for providing electrical power to the apparatus;

a second section of generally cylindrical shape having means for generating and transmitting a magnetic field through portions of the pipeline wall adjacent the section and means for sensing magnetic flux leakage caused by anomalies in the pipeline wall;

a third section of generally cylindrical shape having means for storing data retrieved by the apparatus;

a plurality of bars disposed circumferentially around the second section, each bar flexibly mounted on the second section to allow the bar to move radially inwardly and radially outwardly to provide clearance for the apparatus in the event that it encounters obstructions as it travels through the pipeline;

means mounted on the bars for generating and transmitting a magnetic field through portions of the pipeline wall adjacent the second section;

means mounted on the bars for measuring magnetic flux leakage adjacent the second section caused by anomalies in the pipeline wall;

means for supporting the sections in relation to the pipeline wall;

means for propelling the sections through the pipeline;

means for transmitting the magnetic flux leakage measurements to the data storage means;

a plurality of wheels mounted on the bars adjacent the magnetic field generating means for bearing against the pipeline wall as the apparatus moves through the pipeline so as to reduce wear on the magnetic field generating means and the magnetic flux leakage measuring means; and wherein adjacent sections are connected by flexible links so as to permit movement of the apparatus through bends and restrictions in the pipeline.

* * * * *